United States Patent
Corrigan, Jr.

(10) Patent No.: US 9,526,647 B2
(45) Date of Patent: Dec. 27, 2016

(54) INTERCONNECTION BETWEEN SELECTIVELY-EXPANDABLE AND SELF-EXPANDABLE SECTIONS OF AN OSTIAL STENT

(71) Applicant: Medical Ingenuities, LLC, Wheaton, IL (US)

(72) Inventor: Richard F. Corrigan, Jr., Wheaton, IL (US)

(73) Assignee: Medical Ingenuities, LLC, Wheaton, IL (US)

(*) Notice: Subject to any disclaimer, the term of this patent is extended or adjusted under 35 U.S.C. 154(b) by 8 days.

(21) Appl. No.: 14/260,040

(22) Filed: Apr. 23, 2014

(65) Prior Publication Data

US 2014/0316509 A1 Oct. 23, 2014

Related U.S. Application Data

(60) Provisional application No. 61/815,134, filed on Apr. 23, 2013.

(51) Int. Cl.

| A61F 2/06 | (2013.01) |
|---|---|
| A61F 2/958 | (2013.01) |
| A61F 2/852 | (2013.01) |
| A61F 2/82 | (2013.01) |
| A61F 2/90 | (2013.01) |
| A61F 2/91 | (2013.01) |

(52) U.S. Cl.
CPC .............. *A61F 2/958* (2013.01); *A61F 2/852* (2013.01); *A61F 2/90* (2013.01); *A61F 2/91* (2013.01); *A61F 2002/821* (2013.01); *A61F 2002/9583* (2013.01); *A61F 2250/0048* (2013.01)

(58) Field of Classification Search
CPC ........................... A61F 2/852; A61F 2002/821
See application file for complete search history.

(56) References Cited

U.S. PATENT DOCUMENTS

| 5,607,444 A | 3/1997 | Lam |
| 5,843,158 A | 12/1998 | Lenker et al. |
| 5,938,697 A | 8/1999 | Killion et al. |

(Continued)

FOREIGN PATENT DOCUMENTS

| KR | 20110037235 A | 4/2011 |
| WO | 2005046526 A1 | 5/2005 |

OTHER PUBLICATIONS

International Search Report and Written Opinion from PCT/US2014/035192 entitled: Interconnection Between Selectively—Expandable and Self-Expandable Sections of an Ostial Stent (Dated Apr. 23, 2014).

(Continued)

*Primary Examiner* — Brian Dukert
(74) *Attorney, Agent, or Firm* — Hovey Williams LLP

(57) ABSTRACT

An ostial stent is operable to be placed at the ostium of a patient's vascular system so as to improve vessel patency in the ostial region. The ostial stent includes a stent tube that presents spaced apart proximal and distal stent openings and a longitudinal stent passage that extends between the openings. The stent tube includes a selectively-expandable tube section and a self-expandable tube section. The self-expandable tube section projects longitudinally from one of the stent openings, and is automatically expandable to a flared condition for placement within the ostium.

12 Claims, 11 Drawing Sheets

(56) References Cited

U.S. PATENT DOCUMENTS

| | | |
|---|---|---|
| 6,096,071 A | 8/2000 | Yadav |
| 6,159,238 A | 12/2000 | Killion et al. |
| 6,168,621 B1 | 1/2001 | Vrba |
| 6,315,708 B1 | 11/2001 | Salmon et al. |
| 6,409,755 B1 | 6/2002 | Vrba |
| 6,485,509 B2 | 11/2002 | Killion et al. |
| 6,517,570 B1 | 2/2003 | Lau et al. |
| 6,740,113 B2 | 5/2004 | Vrba |
| 7,037,327 B2 | 5/2006 | Salmon et al. |
| 7,112,217 B1 | 9/2006 | Kuglar et al. |
| 7,147,658 B2 | 12/2006 | Vrba |
| 7,455,688 B2 | 11/2008 | Furst et al. |
| 7,632,302 B2 * | 12/2009 | Vreeman ................ A61F 2/915 623/1.15 |
| 2005/0154447 A1 | 7/2005 | Goshgarian |
| 2006/0206189 A1 | 9/2006 | Furst et al. |
| 2007/0021828 A1 | 1/2007 | Krolik et al. |
| 2007/0038282 A1 | 2/2007 | Vrba |
| 2007/0038283 A1 | 2/2007 | Mustapha |
| 2007/0123972 A1 | 5/2007 | Greenberg et al. |
| 2007/0173921 A1 | 7/2007 | Wholey et al. |
| 2008/0208322 A1 | 8/2008 | Sandhu |
| 2012/0245673 A1 | 9/2012 | Ma et al. |
| 2013/0030513 A1 | 1/2013 | Corrigan, Jr. et al. |

OTHER PUBLICATIONS

"Cordis Precise (TM) OTW Nitinol System", US FDAwebsite: http://www.fda.gov/MedicalDevices/ ProductsandMedicalProcedures/DeviceApprovalsandClearances/ Recently-ApprovedDevices/ucm077440.htm: (published at least as early as Jun. 8, 2010).

* cited by examiner

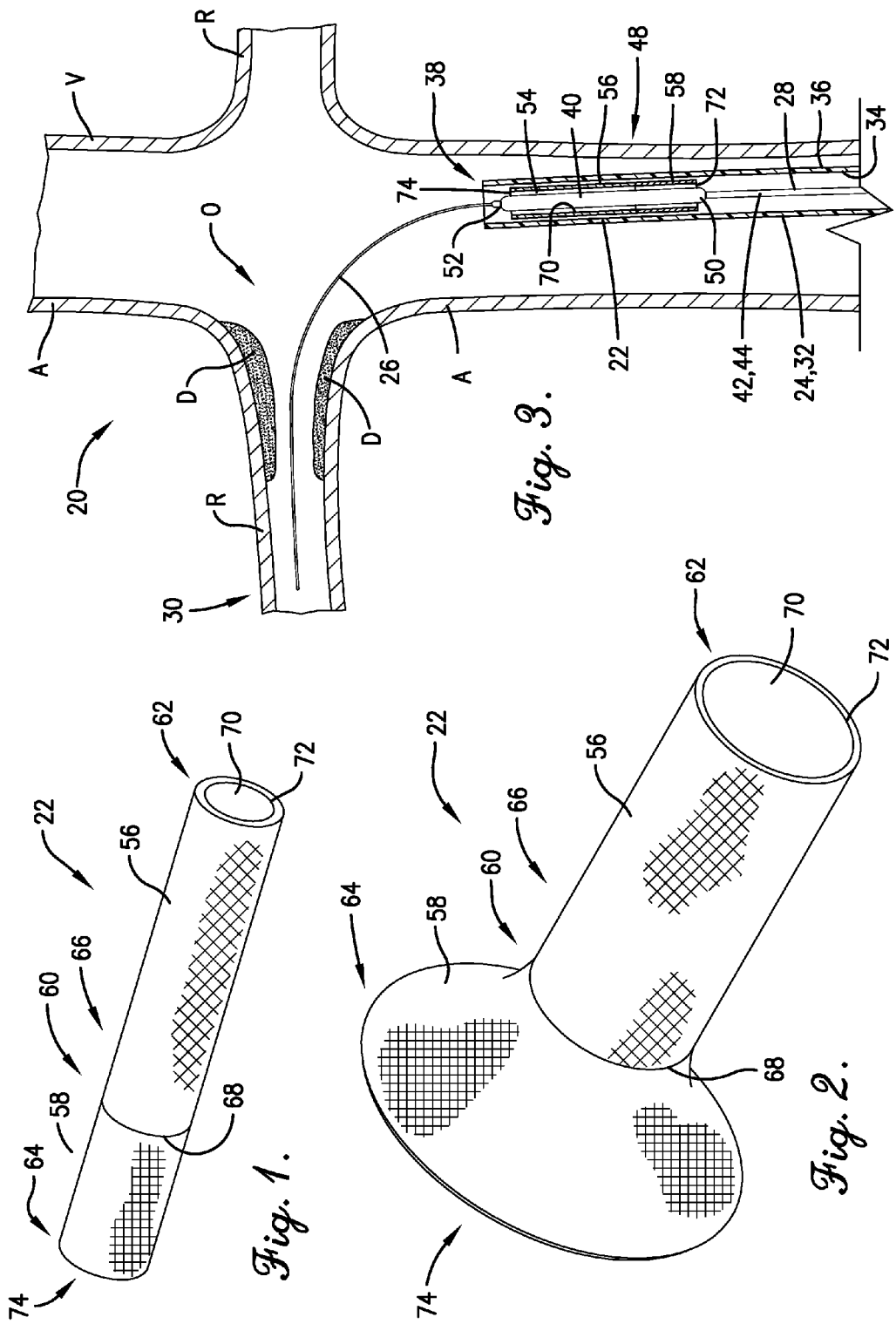

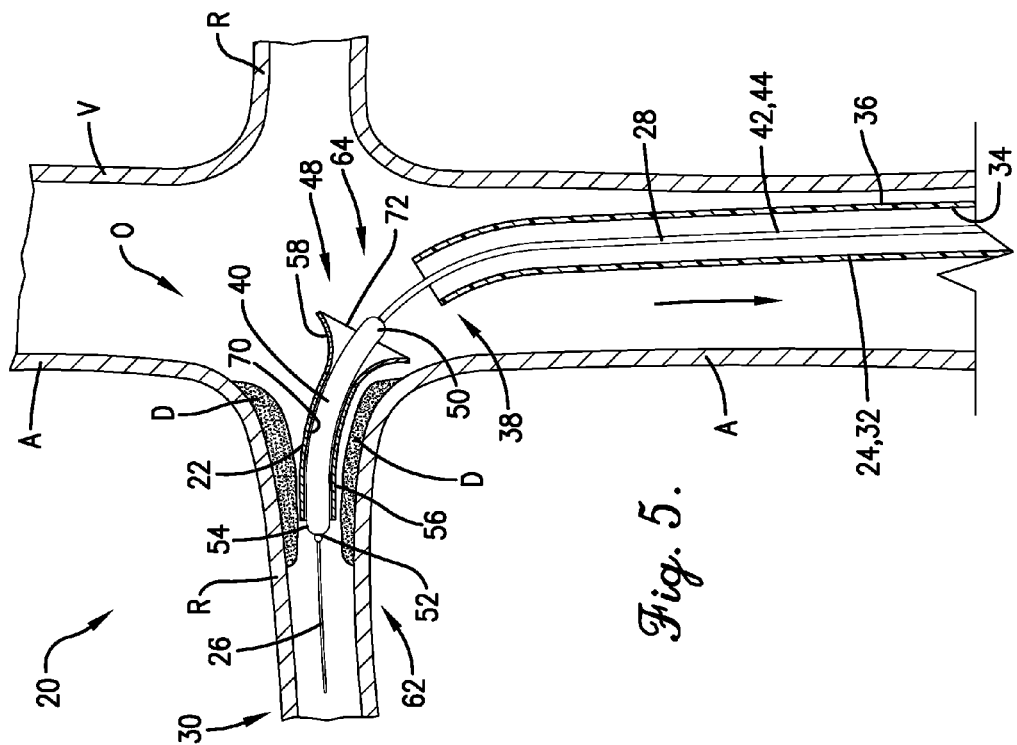
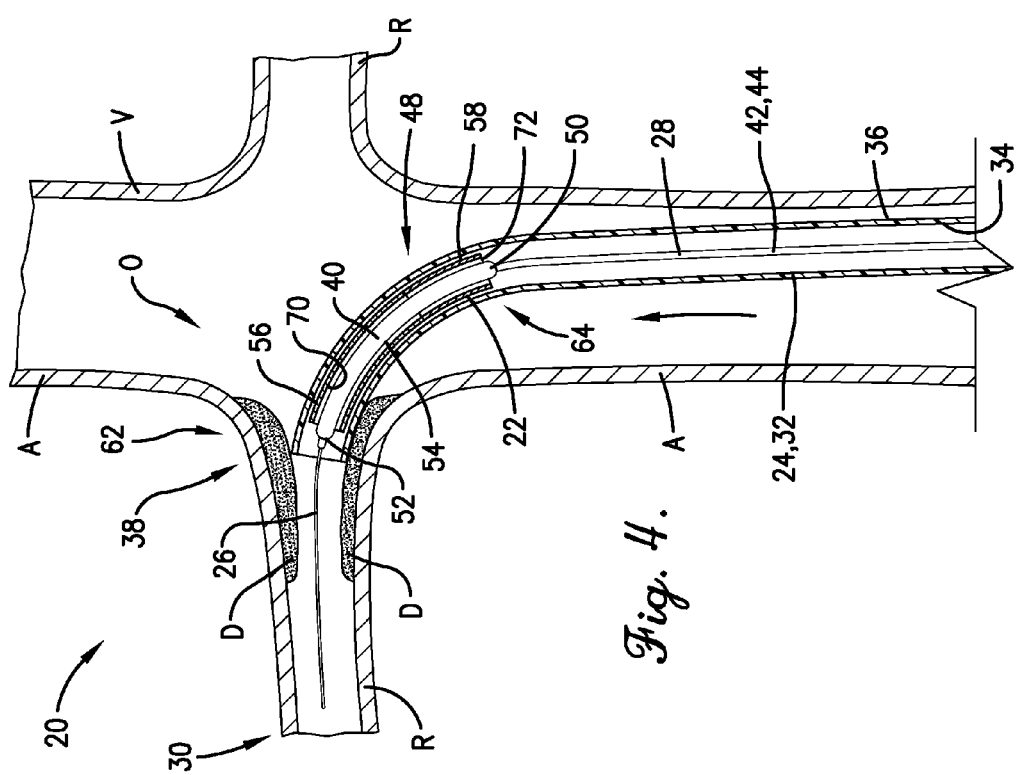

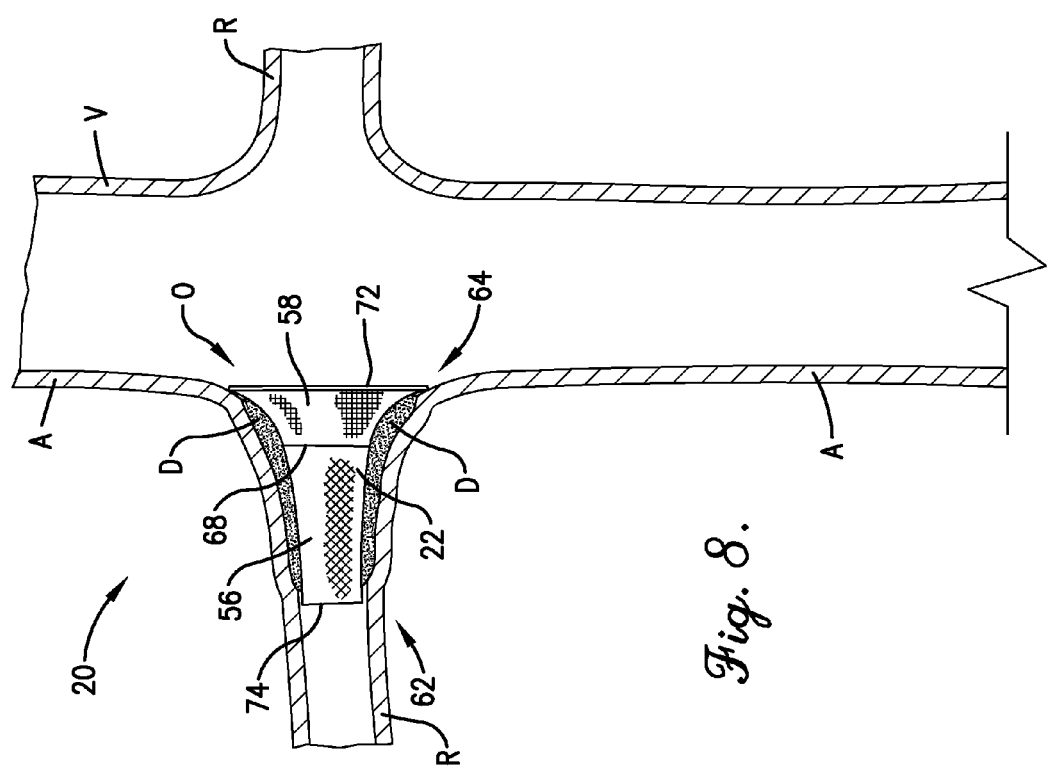

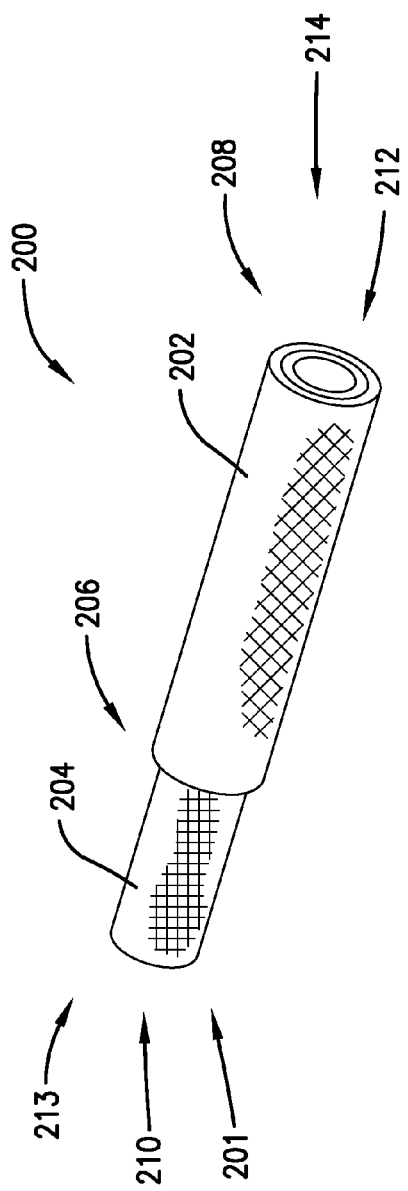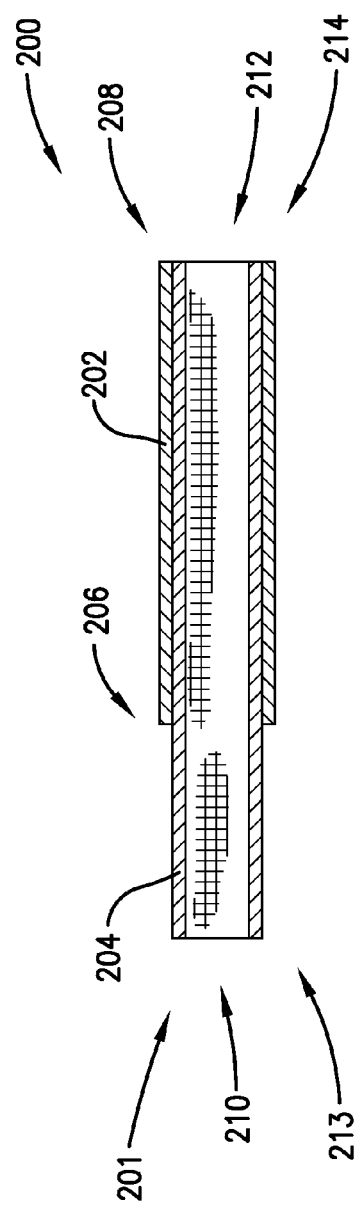

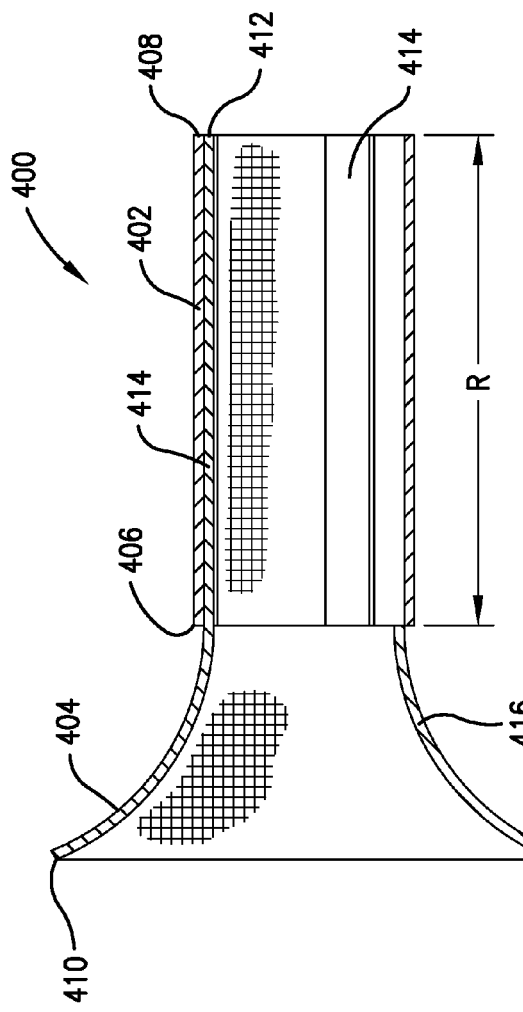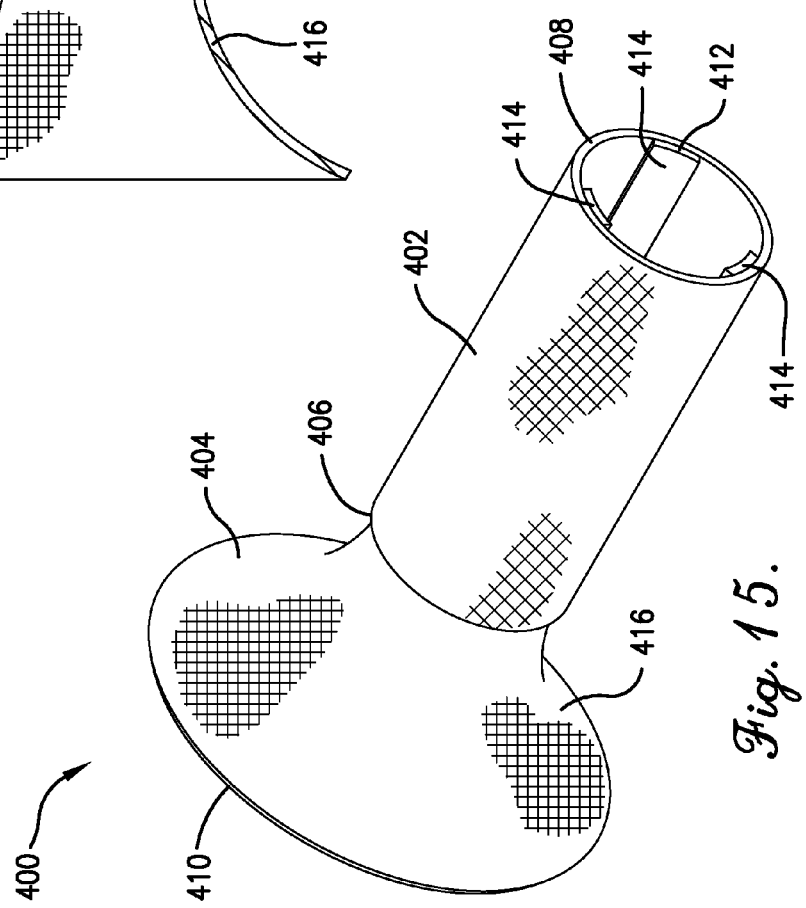

INTERCONNECTION BETWEEN SELECTIVELY-EXPANDABLE AND SELF-EXPANDABLE SECTIONS OF AN OSTIAL STENT

RELATED APPLICATION

This application claims the benefit of U.S. Provisional Application Ser. No. 61/815,134, filed Apr. 23, 2013, entitled OSTIAL STENT WITH OVERLAPPING STENT SECTION, which is hereby incorporated in its entirety by reference herein.

BACKGROUND

1. Field

The present invention relates generally to stents for placement within the vascular system. More specifically, embodiments of the present invention concern an ostial stent with a selectively-expandable tube section and a self-expandable tube section.

2. Discussion of Prior Art

Stents have long been used to improve the patency of occluded vessels. In one conventional form, balloon-expandable stents are typically made of a relatively strong metal, such as stainless steel, and/or a bioabsorbable material. This type of stent is used in vessels where greater radial strength is required. Furthermore, balloon-expandable stents are normally used in areas where the stent is unlikely to be crushed, e.g., by bending/crushing through contact with muscle or other tissues. In another conventional form, self-expanding stents are made of a relatively flexible shape memory alloy material. This type of stent is used where greater flexibility of the stent is required. Conventional stents are sometimes deployed to expand an ostial region. In order to support the ostium, the stent is positioned to extend out into the larger vessel. The protruding portion of the stent is then flared to apply pressure to and support the ostium.

Prior art stents suffer from various undesirable limitations. Conventional stents are not well suited for precise placement in ostial regions of a patient's vascular system so as to conform to the ostial flaring of the larger vessel, particularly in the ostium region between the aorta and renal artery. For instance, balloon-expandable stents are difficult to precisely position in such an ostial region because of artery movement due to beating of the heart and patient breathing. Furthermore, precise positioning is difficult because such stents are slightly radiopaque and, therefore, can be difficult to view during positioning. Even when properly positioned, it may be necessary to flare the proximal end of the stent with the balloon catheter, which can be difficult. Self-expanding shape memory alloy (SMA) stents are deficient in some applications because such stents have less radial strength than balloon-expandable stents. Additionally, SMA stents are less radiopaque than balloon-expandable stents.

SUMMARY

The following brief summary is provided to indicate the nature of the subject matter disclosed herein. While certain aspects of the present invention are described below, the summary is not intended to limit the scope of the present invention.

Embodiments of the present invention provide an ostial stent system that does not suffer from the problems and limitations of the prior art stents set forth above.

A first aspect of the present invention concerns an ostial stent for placement at the ostium of a patient's vascular system so as to improve vessel patency in the ostial region. The ostial stent broadly includes a stent tube. The stent tube presents spaced apart proximal and distal stent openings and a longitudinal stent passage that extends between the openings. The stent tube includes a selectively-expandable tube section and a self-expandable tube section. The self-expandable tube section projects longitudinally from one of the stent openings, and is automatically expandable to a flared condition for placement within the ostium. The tube sections are partly overlapped and interconnected along an overlapping region. The overlapping region is spaced longitudinally from the one stent opening, such that the self-expandable tube section is at least partly outside the overlapping region.

A second aspect of the present invention concerns an ostial stent for placement at the ostium of a patient's vascular system so as to improve vessel patency in the ostial region. The ostial stent broadly includes a stent tube and stent connection structure. The stent tube presents spaced apart proximal and distal stent openings and a longitudinal stent passage that extends between the openings. The stent tube includes a selectively-expandable tube section and a self-expandable tube section. The self-expandable tube section projects longitudinally from one of the stent openings, and is automatically expandable to a flared condition for placement within the ostium. The tube sections are arranged in an end-to-end to configuration to define a connection location spaced between the stent openings. The stent connection structure interconnects the tube sections at the connection location. The stent connection structure spans between the tube sections and is formed of a material dissimilar from that of the tube sections.

A third aspect of the present invention concerns an ostial stent system operable to improve vessel patency in the ostial region of a patient's vascular system. The ostial stent system broadly includes a stent tube and an elongated inflatable balloon. The stent tube presents spaced apart proximal and distal stent openings and a longitudinal stent passage that extends between the openings. The stent tube includes a balloon-expandable tube section and a self-expandable tube section. The balloon-expandable tube section presents opposite longitudinally spaced apart ends and a midpoint spaced equally therebetween. The self-expandable tube section projects longitudinally from one of the stent openings. The self-expandable tube section is being automatically expandable to a flared condition for placement within the ostium. The system further includes an elongated inflatable balloon temporarily received in the stent passage. The presents opposite longitudinally spaced apart balloon ends and a balloon midpoint spaced equally therebetween. The balloon midpoint is located closer to the self-expandable tube section than the midpoint of the balloon-expandable tube section.

Other aspects and advantages of the present invention will be apparent from the following detailed description of the preferred embodiments and the accompanying drawing figures.

BRIEF DESCRIPTION OF THE DRAWING FIGURES

Preferred embodiments of the invention are described in detail below with reference to the attached drawing figures, wherein:

FIG. 1 is a perspective of an ostial stent for use as part of an ostial stent system constructed in accordance with a preferred embodiment of the present invention, with the ostial stent including a self-expandable SMA proximal tube section and a balloon-expandable distal tube section joined end-to-end, where the tube sections are made from laser-cut tube material shown schematically, and showing the ostial stent in a radially contracted condition where the tube sections present inner and outer tube diameters that are substantially continuous along the length of the stent;

FIG. 2 is a perspective of the ostial stent shown in FIG. 1, showing the ostial stent in a memory flared condition where the inner and outer tube diameters of the proximal tube section increase in the proximal direction;

FIG. 3 is a schematic view of the ostial stent system inserted in a patient's vascular system, with a fragmentary cross-section of the vascular system taken along a generally longitudinal plane to show the aorta and opposite renal arteries extending laterally to intersect the aorta along respective ostial regions, where one of the ostial regions has deposits therein, with the ostial stent system including the ostial stent, a guide catheter/sheath, a guide wire, and a balloon catheter assembly, showing the guide wire extending upwardly into the renal artery, and showing the remaining components of the ostial stent system in a pre-insertion position so that the ostial stent is located in the aorta adjacent the ostial region;

FIG. 4 is a schematic view of the ostial stent system similar to FIG. 3, but showing the ostial stent, guide catheter/sheath, and balloon catheter assembly shifted so that the distal end of the guide catheter is located in the ostial region in a stent-insertion position;

FIG. 5 is a schematic view of the ostial stent system similar to FIG. 4, but showing the guide catheter/sheath retracted proximally from the stent-insertion position to expose the ostial stent, and showing the ostial stent and balloon catheter assembly shifted distally along the guide wire and into the ostial region, with the proximal tube section being expanded from the radially contracted condition toward a flared condition, where the diameter of the proximal tube section increases in the proximal direction;

FIG. 6 is a schematic view of the ostial stent system similar to FIG. 5, but showing distal and proximal ends of the balloon partly expanded and positioned outside of the ostial stent, with the partly expanded proximal balloon end operating to restrict the ostial stent from moving proximally relative to the balloon;

FIG. 7 is a fragmentary schematic view of the ostial stent system similar to FIG. 5, but showing the ostial stent and balloon catheter assembly shifted further distally along the guide wire and into the ostial region, with the proximal balloon end and the proximal tube section being further expanded toward the flared condition, and with the proximal tube section engaging the ostial opening by contacting the wall of the aorta so as to restrict further distal advancement of the stent;

FIG. 8 is a fragmentary schematic view of the ostial stent system similar to FIG. 6, but showing the ostial stent shifted further distally into the ostial region, with the proximal and distal tube sections being expanded to contact and expand the adjacent deposits within the corresponding ostial region;

FIG. 9 is a perspective of an ostial stent for use as part of an ostial stent system and constructed in accordance with a second preferred embodiment of the present invention, with the ostial stent including a self-expandable SMA proximal tube section and a balloon-expandable distal tube section that receives the proximal tube section, where the tube sections are preferably made from laser-cut tube material shown schematically, and showing the ostial stent in a radially contracted condition where the tube sections present inner and outer tube diameters;

FIG. 10 is a longitudinal cross section of the ostial stent shown in FIG. 8, showing a portion of the proximal tube section as being coextensive with the distal tube section and the distal tube section fully radially overlapping the portion of the proximal tube section;

FIG. 15 is a perspective of an ostial stent constructed in accordance with a fourth preferred embodiment of the present invention, with the ostial stent including a self-expandable SMA proximal tube section with multiple longitudinally-extending legs and a balloon-expandable distal tube section that receives the legs of the proximal tube section;

FIG. 16 is a longitudinal cross section of the ostial stent shown in FIG. 15, showing the proximal tube section extending part of the length of the distal tube section;

Figure 19:
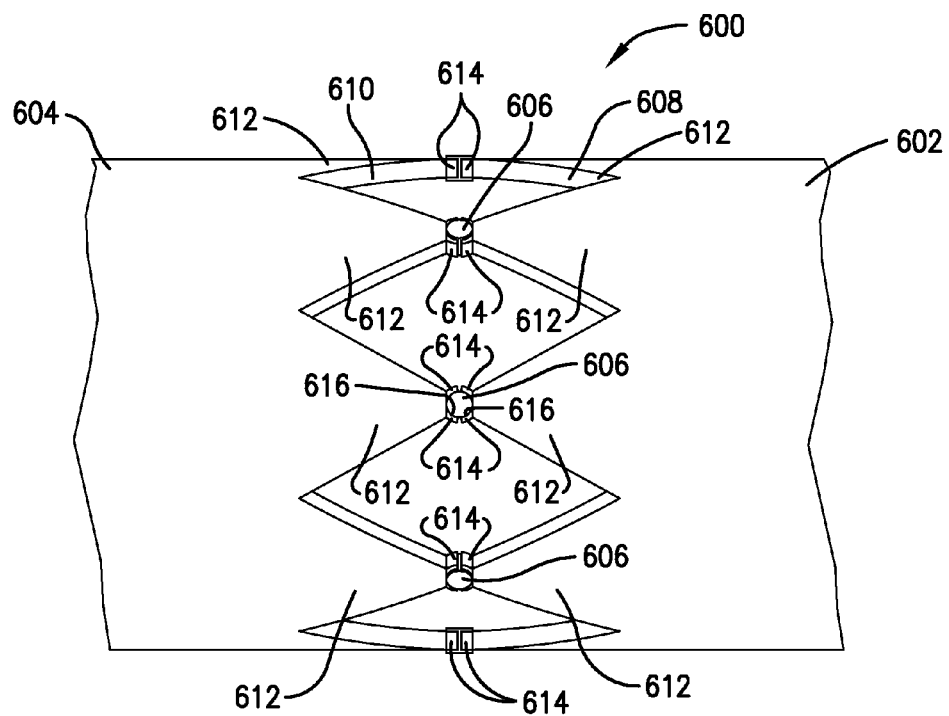
Figure 20:
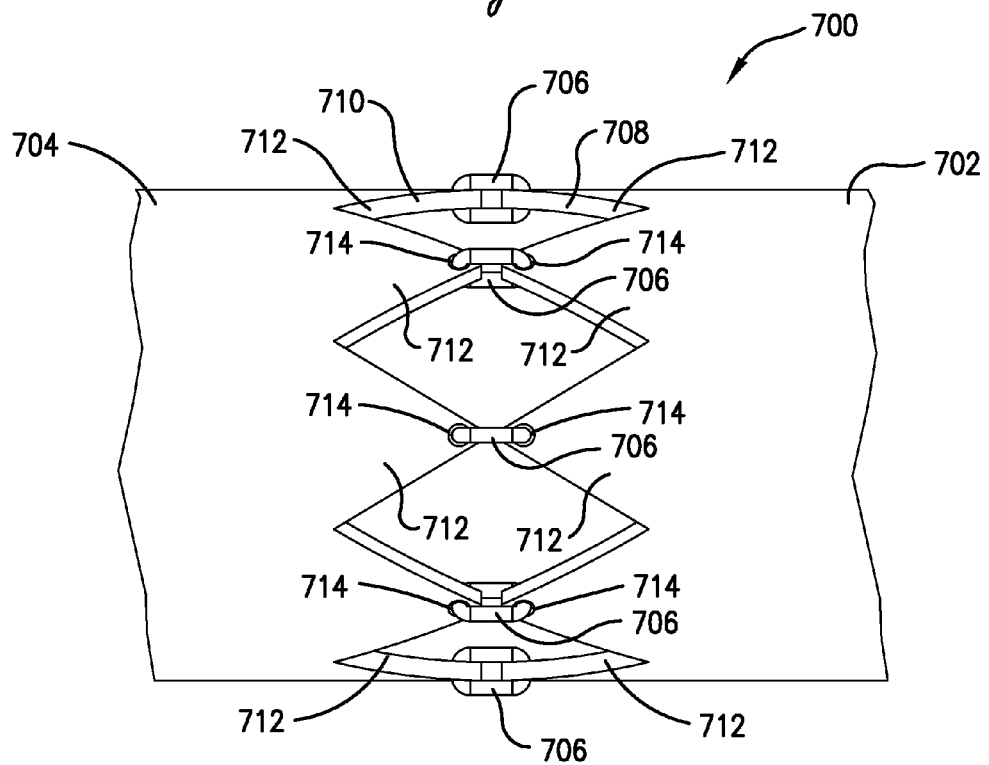
Figure 21:
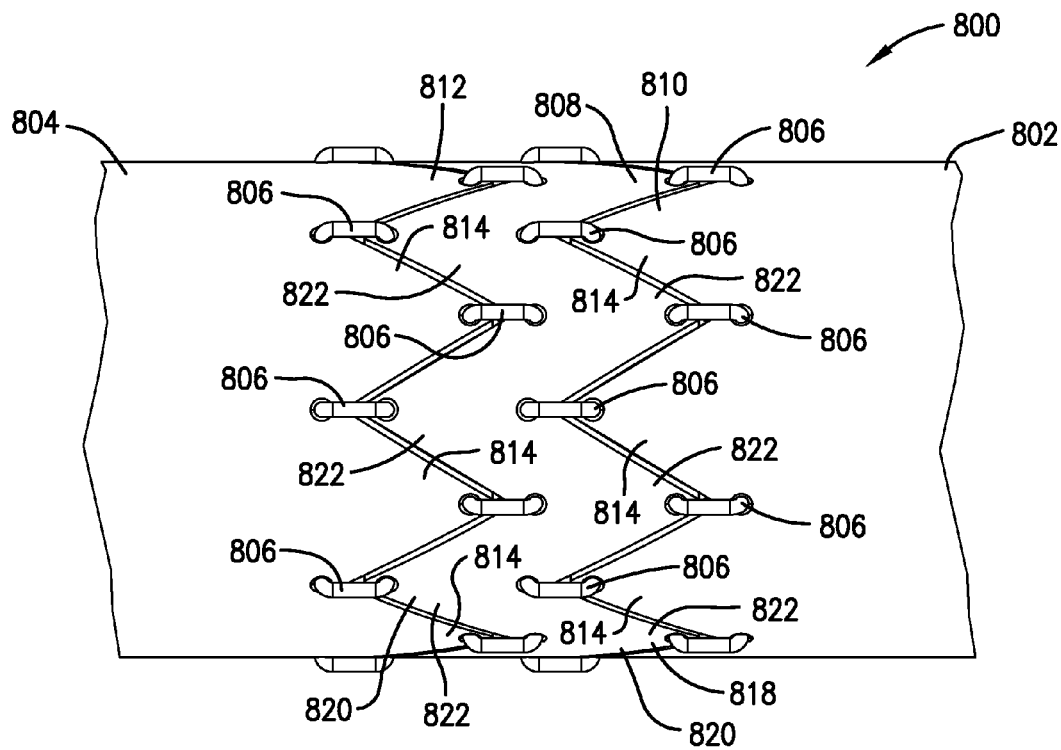
Figure 22:
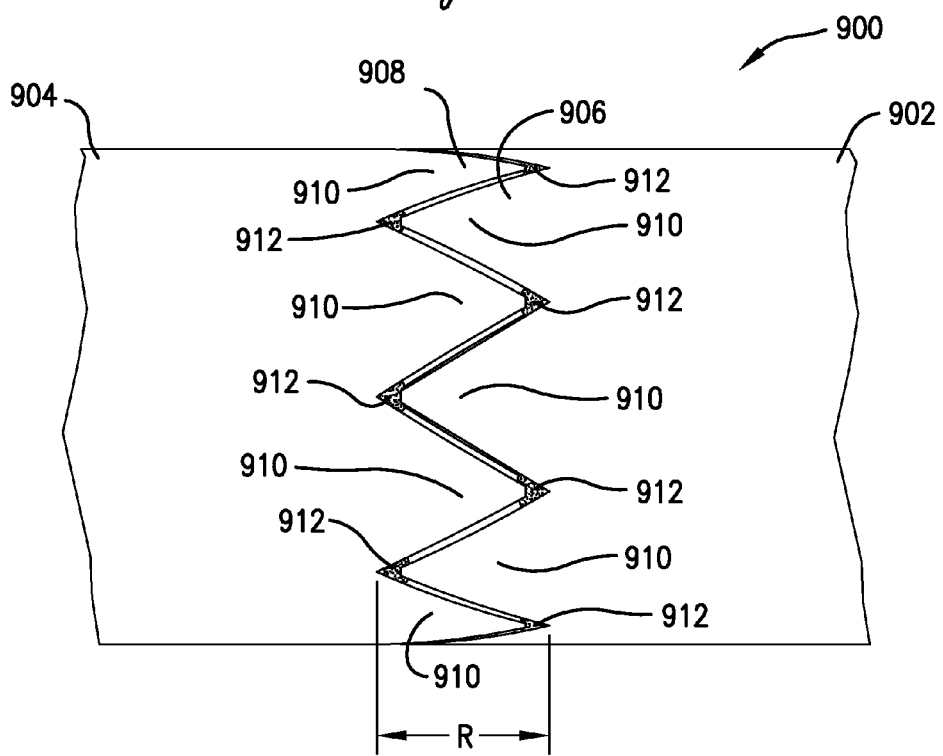

FIG. 19 is a fragmentary side elevation of an ostial stent constructed in accordance with a sixth preferred embodiment of the present invention, with the ostial stent including a self-expandable SMA proximal tube section, a balloon-expandable distal tube section, and circular connection disks, where each the tube sections include arms that do not radially overlap one another and are welded to the disks;

FIG. 20 is a side elevation of an ostial stent constructed in accordance with a seventh preferred embodiment of the present invention, with the ostial stent including a self-expandable SMA proximal tube section, a balloon-expandable distal tube section, and stitches to secure the tube sections to one another;

FIG. 21 is a fragmentary side elevation of an ostial stent constructed in accordance with an eighth preferred embodiment of the present invention, with the ostial stent including a self-expandable SMA proximal tube section, a balloon-expandable distal tube section, an intermediate tube section, and stitches to secure the intermediate tube section to the proximal ad distal tube sections; and FIG. 22 is a fragmentary side elevation of an ostial stent constructed in accordance with a ninth preferred embodiment of the present invention, with the ostial stent including a self-expandable SMA proximal tube section and a balloon-expandable distal tube section welded to one another.

The drawing figures do not limit the present invention to the specific embodiments disclosed and described herein. The drawings are not necessarily to scale, emphasis instead being placed upon clearly illustrating the principles of the preferred embodiments.

DETAILED DESCRIPTION OF THE PREFERRED EMBODIMENTS

Turning initially to FIGS. 1, 2, and 3, an ostial stent system 20 is constructed in accordance with a preferred embodiment of the present invention. The ostial stent system 20 is preferably used to implant an ostial stent 22 in an ostial region O of a patient's vascular system and thereby improve vessel patency in the ostial region. As used herein, the term "ostial region" refers to a junction between two vessels. One such junction includes an ostium, which is normally the mouth of the smaller of the two vessels.

As will be discussed further, it has been found that the illustrated system 20 provides for simple and accurate stent implantation in the ostial region. More particularly, the system 20 restricts the operator from advancing the stent too far into the ostium. At the same time, the system 20 signals the operator that the stent has been sufficiently advanced into the ostium. The ostial stent system 20 broadly includes the ostial stent 22, a guide catheter/sheath 24, a guide wire 26, and a balloon catheter assembly 28.

The illustrated embodiment has been depicted in use with ostial region O defined by the aorta A and renal arteries R that carry blood from the aorta A to kidneys (not shown). However, the principals of the present invention are equally applicable to other ostial regions within the vascular system V. Returning to the illustrated arrangement, each of the renal arteries R presents a corresponding ostium O between the artery R and aorta A. Generally, the aorta A has a lumen diameter that ranges from about twenty-five (25) millimeters to about thirty-five (35) millimeters. The renal arteries R generally have a lumen diameter that ranges from about four (4) millimeters to about ten (10) millimeters. The inner annular surface of the left ostium O has a plaque deposit D thereon. The deposit D reduces the diameter of the ostium O and undesirably restricts blood flow through the ostium O. Again, the illustrated system 20 is preferably used in the illustrated ostial region O between the aorta A and renal arteries R. However, it is also within the ambit of the present invention to use the system 20 to improve blood flow at other ostial regions in the vascular system V.

Turning to FIGS. 3-5, the ostial stent system 20 is operable to position the stent 22 by initially inserting the guide wire 26 within the patient. The guide wire 26 is a conventional guide wire that extends continuously to a distal end 30. In the usual manner, the guide wire 26 is used to direct the other components of the ostial stent system 20 along the aorta A and into position along the ostial region.

The guide catheter/sheath 24 is conventional and preferably includes a continuous catheter tube 32 that presents a guide lumen 34, an outer tube surface 36, and a distal end 38, with the guide lumen 34 extending continuously from a proximal tube end (not shown) to the distal end 38. As will be described, the guide catheter/sheath 24 is preferably sized and configured so that the guide lumen 34 can slidably receive the ostial stent 22, guide wire 26, and the balloon catheter assembly 28.

The balloon catheter assembly 28 is also conventional and includes a balloon 40 and a balloon catheter 42. The balloon catheter 42 includes a continuous catheter tube 44 that presents a lumen (not shown), an outer surface, and a distal end 48. The balloon 40 is inflatable and presents proximal and distal ends 50,52, with an outer balloon surface 54 extending between the ends 50,52. The proximal end 50 of the balloon 40 is attached adjacent the distal end 48 of the balloon catheter 42.

The guide catheter/sheath 24 and balloon catheter assembly 28 are both slidably received on the guide wire 26, with the balloon catheter assembly 28 being positioned within the guide lumen 34. Thus, the guide catheter/sheath 24 and balloon catheter assembly 28 are each slidable along the length of the guide wire 26.

The ostial stent 22 is configured for use in the illustrated vascular system V to improve vessel patency in the ostial region O. While the illustrated ostial stent 22 is preferably used between the aorta A and renal artery R, it is also within the ambit of the present invention to use the ostial stent 22 to improve blood flow at other ostial regions in the vascular system V.

The ostial stent 22 preferably includes a balloon-expandable distal tube section 56 and a self-expandable proximal tube section 58 attached end-to-end and/or in overlapping engagement with one another. As will be shown in subsequent embodiments, the tube sections can be interconnected by a stent connection structure, such as stitches or a weld disk. As will be discussed in greater detail, the ostial stent 22 is flared along the axis thereof to distend the ostial region O.

The distal tube section 56 extends continuously between proximal and distal ends 60,62 thereof (see FIGS. 1 and 2). Also, the distal tube section 56 presents inner and outer distal tube diameter dimensions. The distal tube section 56 is preferably formed from laser-cut metal tube so that the distal tube section 56 can be selectively expanded using a balloon (or another suitable stent-expanding device). However, it is also within the scope of the present invention where the distal tube section 56 is formed from other suitable materials, such as woven metal fabric, braided wire, welded wire coils, or molded or extruded materials. The distal tube section 56 preferably includes stainless steel, but could include other metallic or nonmetallic materials. For instance, the distal tube section 56 could include chromium-cobalt, Nitinol (which is preferably not heat treated to pre-shape the material, as described below), Nuloy, a bioabsorbable polymer (e.g., a polymer including polylactic acid, poly-L-lactic acid, or polymer combinations), a biocorrodable metal (such as zinc, iron, or magnesium), or a combination thereof, without departing from the scope of the present invention. The distal tube section 56 is preferably shiftable from a radially contracted condition (see FIG. 1) to a radially expanded condition (see FIG. 2). In the radially contracted condition, the outer tube diameter dimension of the tube section 56 is substantially constant along the tube length and preferably ranges from about two (2) millimeters to about four (4) millimeters. In the radially expanded condition, the distal tube section 56 has an enlarged outer tube diameter dimension that preferably ranges from about four (4) millimeters to about ten (10) millimeters. However, it is within the ambit of the present invention where the distal tube section has an outer tube diameter dimension that falls outside of one or both of these ranges.

The proximal tube section 58 extends continuously between proximal and distal ends 64,66 and presents inner and outer proximal tube diameter dimensions (see FIGS. 1 and 2). The proximal tube section 58 is also preferably formed of a laser-cut metal tube. However, the principles of the present invention are applicable to the proximal tube section 58 being formed of other suitable materials, such as woven metal fabric, braided wire, welded wire coils, or molded or extruded materials. The laser-cut metal tube permits expansion and contraction of the proximal tube section 58, as will be discussed. As will be shown in subsequent embodiments, the proximal tube section 58 can be secured to the distal tube section 56 using a variety of techniques, including overlap between the sections 56,58 or various connection structure (e.g., woven fabric, interconnecting segments, etc.).

The metal material of the proximal tube section 58 preferably includes an SMA material. More preferably, the proximal tube section 58 is formed of nickel-titanium (i.e., Nitinol). However, the principles of the present invention are applicable where the proximal tube section 58 includes copper-zinc-aluminum-nickel, copper-aluminum-nickel, or combinations of the referenced SMA materials.

The tube sections 56,58 are initially cut from cylindrical tube stock (not shown). Preferably, the tube sections 56,58 are cut so that the distal tube section 56 presents a distal tube length dimension that is longer than a proximal tube length dimension presented by the proximal tube section 58. However, for some aspects of the present invention, the tube sections 56,58 could be manufactured with alternative tube lengths (e.g., the tube lengths could be the same).

In the present embodiment, the tube sections are joined end-to-end by attaching the distal end 66 of the proximal tube section 58 to the proximal end 60 of the distal tube section 56. The principles of the present invention are equally applicable where various types of welding or joining methods are employed for suitably interconnecting tube sections 56,58, including those methods disclosed in subsequently described embodiments. Thus, the tube sections 56,58 cooperatively define a passage 70 that extends continuously between proximal and distal openings 72,74 of the ostial stent 22. In the illustrated embodiment, the overall length of the ostial stent 22 preferably ranges from about ten (10) millimeters to about twenty-five (25) millimeters. However, it is also within the scope of the present invention where the ostial stent 22 has an overall length that falls outside of this range.

The proximal tube section 58 is preferably formed of Nitinol so that the proximal tube section 58 can be sufficiently expanded to at least conform to the shape of the associated vascular structure and, more preferably, even slightly distend the ostial region O. As will be discussed, the proximal tube section 58 preferably self-expands from a radially contracted condition (see FIG. 1) to a memory flared condition (see FIG. 2) when located adjacent the ostial region O. In the radially contracted condition, the outer tube diameter dimension of the proximal tube section 58 is preferably substantially the same as the distal tube section 56. In the memory flared condition, the outer tube diameter dimension of proximal tube section 58 preferably ranges from about four (4) millimeters to about ten (10) millimeters. More specifically, in the memory flared condition, the distal end 66 of tube section 58 has an outer diameter dimension that is preferably much smaller than the proximal end 64. Preferably, the outer diameter dimension flares continuously outwardly from the distal end 66 to the proximal end 68 so that the tube section 58 has a sleeve shape that curves along the length thereof. For some aspects of the present invention, the proximal tube section 58 could have alternative dimensions and/or an alternative shape for suitable use of the ostial stent 22.

As discussed above, the tube section 58 is preferably flared outwardly toward the proximal end 64 so that the proximal end 64 engages the ostium O. This flared shape provides numerous benefits. For instance, the flared stent shape conforms closely to the shape of the vasculature, particularly the ostium O. As a result, the flared end is configured to engage and buttress the ostial wall while restricting inadvertent stent movement into or out of the ostium O. The flared end of stent 22 restricts the operator from advancing the stent too far into the ostium O. Also, through contact with the ostium O, the flared end of stent 22 signals the operator that the stent has been sufficiently advanced into the ostium O. Thus, the flared stent end provides for accurate and simplified stent placement. Consequently, stent implantation procedures can be performed in a shorter period of time. Furthermore, such procedures can reduce the need for implantation of multiple stents in the ostium O due to inaccurate stent placement.

The illustrated proximal tube section 58 is configured for automatic self-expansion in the ostial region O by a process of pre-shaping the proximal tube section 58. For instance, the proximal tube section 58 can be placed in a mold at high temperature and formed into a flared pre-expanded tube shape (not shown) while the Nitinol material is in a high-temperature phase, where the material assumes an Austenite structure. It is also within the ambit of the present invention to use other suitable manufacturing techniques so that the proximal tube section 58 is operable to self-expand when located adjacent the ostial region O. After pre-shaping, the proximal tube section 58 is then permitted to be cooled so as to return to a low-temperature phase, where the material assumes a Martensite structure. In the process of cooling, the tube section 58 self-contracts from the flared pre-expanded tube shape.

The ostial stent 22 is preferably manufactured by initially cutting the tube sections 56,58 to the respective desired lengths from cylindrical tube stock (not shown). Prior to interconnecting the tube sections, the proximal tube section 58 of the ostial stent 22 is preferably pre-shaped, as discussed above, to form the flared pre-expanded tube shape. Again, in the process of cooling to return to the low-temperature phase, the proximal tube section 58 self-contracts from the flared pre-expanded tube shape. After being cooled, the contracted proximal tube section 58 is physically formed to return approximately to the original cylindrical tube shape, with the ostial stent 22 being in the radially contracted condition. This forming step may involve the use of mandrels to roll the proximal tube section back into the original cylindrical tube shape. In this manner, the ostial stent 22 can be subsequently positioned on the balloon and within the guide catheter/sheath 24 (see FIG. 3). The cylindrical tube sections 56,58 are then joined in the end-to-end configuration, although a partially overlapped interconnection may alternative be used, as will subsequently be described.

While not depicted, it is within the ambit of the present invention where the ostial stent 22 includes a fabric cover that extends through the passage 70 and forms the internal surface of the ostial stent 22. Such a fabric cover preferably comprises a woven fabric, where the woven fabric includes a nonmetallic material such as Dacron®, PTFE, or Small Intestine Submucosa (SIS).

Turning to FIGS. 3-7, the system 20 is operable to implant the stent 22 in the ostial region O. Initially, a vascular access site (not shown) is created so that the system 20 can be inserted in the patient. Once the access site is created, the guide wire 26 is inserted and extended into the patient's vascular system V and is positioned along the aorta A so that the distal end 30 can be positioned in the renal artery R. The ostial stent 22 is positioned so that the balloon 40 is received within the ostial stent 22, with the proximal end 50 being located proximally of the proximal end 64 and the distal end 52 being located distally of the distal end 62. Thus, the entire ostial stent 22 is preferably positioned on the balloon 40, with the balloon 40 preferably being slightly longer than the stent 22. Moreover, the illustrated balloon 40 is not centered relative to the distal tube section 56 (i.e., the balloon projects proximally from the distal tube section 56 than the balloon 40 projects distally from the distal tube section 56). It has been determined that this arrangement causes the proximal end 60 of the distal tube section 56 to expand more quickly (or before) the distal end 62 of the distal tube section 56, meaning the stent system 20 is designed so that selectively-expandable tube section 56 expands progressively in the distal direction from the proximal end 60 thereof. It has been determined that this advantage is primarily attributable to the off-centered relationship of the balloon 40 relative to the distal tube section 56. That is, it is not necessary for this aspect of the present invention for the balloon 40 to project beyond the end of the self-expandable tube section 58 of the stent 22.

The ostial stent 22 is positioned within the guide catheter/sheath 24 adjacent the distal end 38 in a covered condition. Thus, the balloon catheter assembly 28, guide catheter/sheath 24, and ostial stent 22 can be cooperatively inserted into the patient's vascular system V and passed along the guide wire 26.

The balloon catheter assembly 28, guide catheter/sheath 24, and ostial stent 22 are located in a pre-insertion position so that the ostial stent 22 is located in the aorta A adjacent the ostial region O (see FIG. 3). This pre-positioning allows the ostial stent 22 to be conveniently shifted into the ostial region O when the doctor selects a preferred moment for stent insertion into the ostium O.

The next step is to shift the balloon catheter assembly 28, guide catheter/sheath 24, and ostial stent 22 along the guide wire 26 so that the distal end 38 of the guide catheter/sheath 24 is located in the ostial region O in a stent-insertion position (see FIG. 4). The distal end 38 of the illustrated guide catheter/sheath 24 is preferably located adjacent the deposits D and within the ostial region O.

From the stent-insertion position, the guide catheter/sheath 24 can be retracted to expose the ostial stent 22 (see FIG. 5). As the guide catheter/sheath 24 is retracted, the guide catheter/sheath 24 no longer restricts self-expansion of the proximal tube section 58. Thus, the proximal tube section 58 begins to automatically self-expand toward the memory flared condition where the diameter of the proximal tube section 58 increases in the proximal direction. This automatic expansion occurs because the SMA material of the proximal tube section 58 is exposed to and heated by the body temperature of the patient. The shape of the proximal tube section 58 in the memory flared condition preferably corresponds to the flared pre-expanded tube shape formed during the pre-shaping process discussed above.

With the guide catheter/sheath 24 being at least partly retracted, the balloon catheter assembly 28 and ostial stent 22 can be moved distally so that the ostial stent 22 is further inserted into the renal artery R. As the stent 22 is moved distally, the proximal tube section 58 is located within and approaches engagement with the ostial region O. At the same time, the proximal tube section 58 continues to automatically self-expand in diameter toward the memory flared condition. Preferably, the stent 22 is positioned, prior to engagement with the renal artery R, so that a proximal portion of the proximal tube section 58 extends into the aorta A. More preferably, the proximal portion extends a length into the aorta A that ranges from about two (2) millimeters to about ten (10) millimeters.

Figure 7:
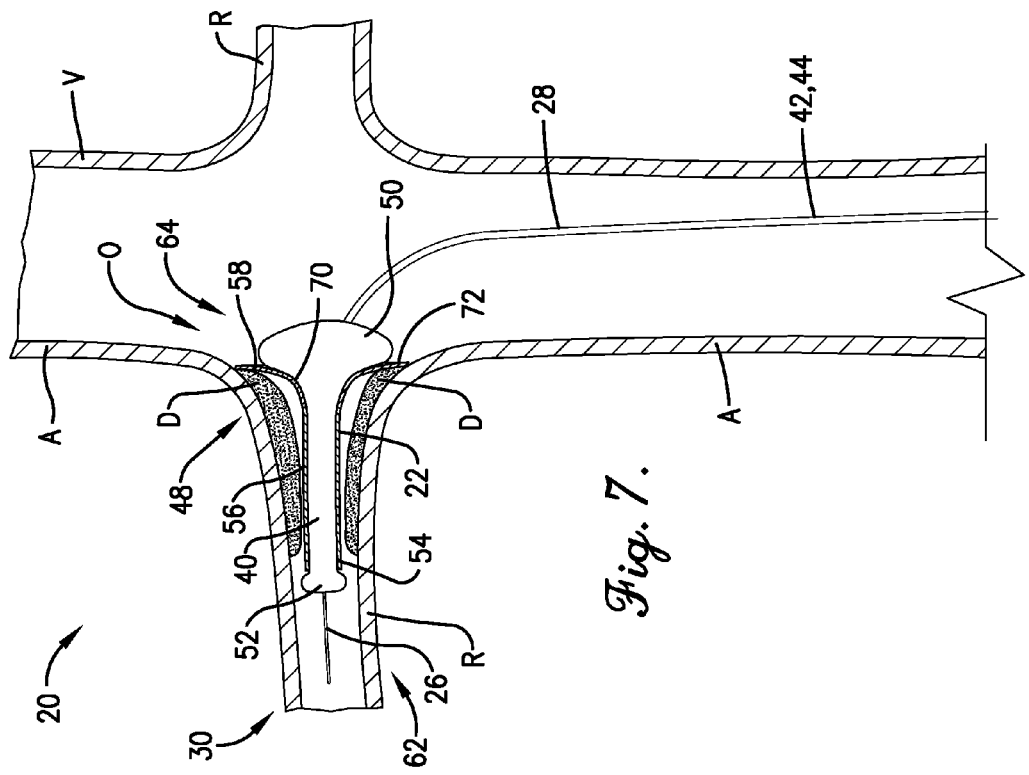
Figure 6:
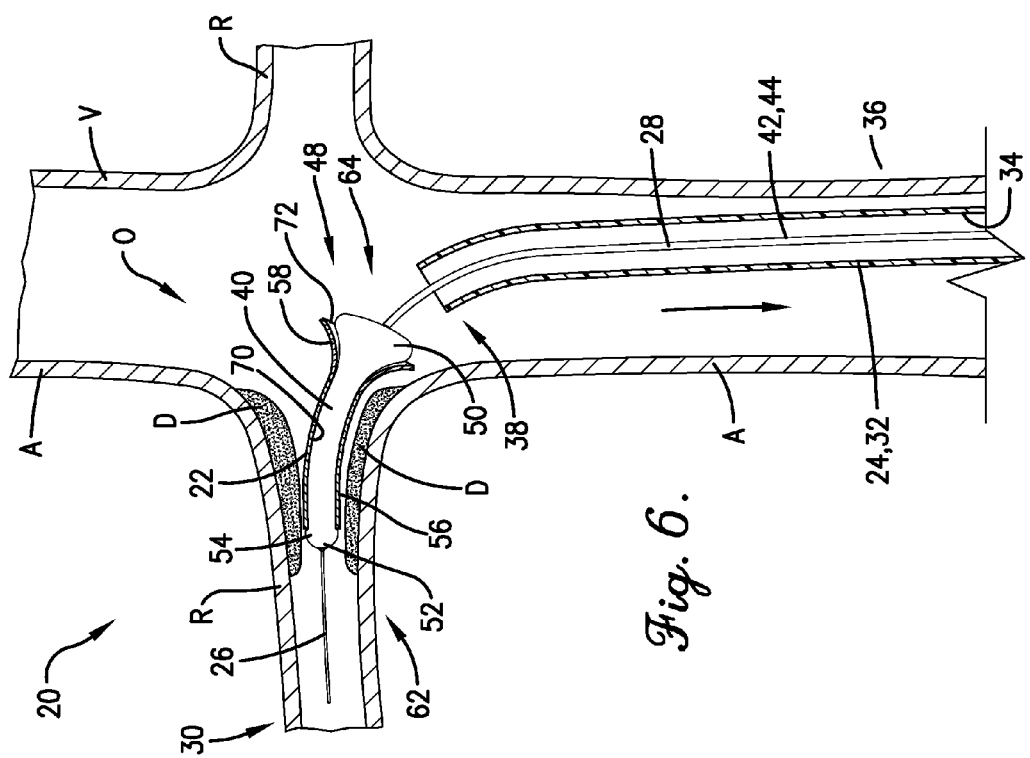

Prior to engagement with the ostial region O, the user can begin inflating the balloon 40 (see FIG. 6). Initial inflation of the balloon 40 causes the distal end 52 and the proximal end 50 of the balloon 40 to be partly expanded outside of the ostial stent 22. The exposed proximal and distal ends 50,52 expand before the part of the balloon 40 within the ostial stent 22 because the ostial stent 22 does not directly engage the balloon ends 50,52. When expanded, the proximal balloon end 50 operates to restrict the ostial stent 22 from moving proximally relative to the balloon 40. That is, the proximal balloon end 50 secures the stent 22 on the balloon 40 so that the balloon 40 is restricted from slipping proximally off the balloon 40 as the stent 22 is inserted into the ostium O. Importantly, it has been found that the partly expanded proximal end 50 serves to wedge the unflared portion of the stent 22 further into the ostium O. Further, as the balloon 40 continues to be inflated, the balloon 40 and the stent 22 will expand in a distal direction from the proximal end 50 to the distal end 22, thus advancing the stent 22 into the appropriate position to cover a stenosis. This is partly attributable to the proximal (SMA) tube section 58 being less restrictive to balloon expansion than the distal tube section 56. Moreover, progressive distal expansion of the stent 22 (particularly for the distal tube section 56) is facilitated by the off-centered relationship (in the proximal direction) of the balloon 40 relative to the distal tube section 56. Furthermore, with the proximal tip 50 of the balloon 40 being enlarged, retrograde proximal shifting of the stent is restricted.

Again, the tube section 58 is preferably flared outwardly toward the proximal end 64 so that the proximal end 64 engages the ostium O. The flared stent shape conforms closely to the region of the ostial wall. As a result, the flared end is configured to engage and buttress the ostial wall while restricting inadvertent stent movement into or out of the ostium O. In particular, the tube section 58 is preferably flared so as to contact the wall of the aorta A adjacent the proximal end 64 (see FIG. 7). In this stent position, engagement of tube section 58 with the aorta A preferably restricts further distal advancement of the stent 22 so that the stent 22 restricts the operator from advancing the stent too far into the ostium O. In engaging the ostium, the flared end of the stent 22 also indicates to the operator that the stent has been sufficiently advanced into the ostium O. Again, these features of the stent permit accurate and simplified stent placement so that stent implantation procedures can be performed in a shorter period of time. Also, such procedures can reduce the need for implantation of multiple stents in the ostium O due to inaccurate stent placement.

The distal tube section 56 is selectively expandable into engagement with the renal artery by expansion from a radially contracted condition (see FIG. 7) to a radially distended condition (see FIG. 8). As used herein, description of the tube section 56 as "selectively expandable" refers to selective expansion of the tube section 56 using a balloon that is inflated manually or by a machine. Preferably, the balloon 40 is inflated to apply an expansion pressure within the distal tube section 56 to provide the desired tube expansion. However, it is also within the ambit of the present invention where another mechanism is employed to expand the distal tube section 56.

Also, the illustrated balloon 40 is selectively manually inflated to apply the expansion pressure. But it is also within the ambit of the present invention where the balloon 40 is selectively inflated using a machine to inflate the balloon 40 (e.g., where the machine can be controlled to inflate the balloon 40 at a user-selected rate of inflation and/or to inflate the balloon to a user-selected pressure). Preferably, the distal tube section 56 has substantially no flaring in the radially distended condition. However, in the expanded condition shown in the drawings (e.g., see FIG. 8), the distal tube section 56 is flared slightly toward the proximal end so as to more closely mimic the vascular shape in which it is positioned.

The illustrated balloon 40 is also preferably used to selectively assist with securement of the proximal tube section 58 by selectively applying an expansion pressure. Without such selective assistance, it is estimated that the proximal tube section 58 expands quickly to about ninety (90) percent of its size when in the flared pre-expanded condition.

It is also within the scope of the present invention where the balloon 40 is not used to selectively assist with complete expansion of the proximal tube section 58. It is particularly noted that such expansion of the stent portion to be located along the flared section of the ostium does not present the same problems as conventional stent designs. With the proximal tube section 58 being already self-expanded, the stent 22 is readily and properly positioned in the ostial region O. Furthermore, with the stent 22 properly positioned, the distal tube section 56 can then be selectively expanded to firmly and securely "lock" the stent 22 into place. Then, if necessary, the balloon catheter assembly 28 can be used to facilitate complete expansion of the proximal tube section 58, without concern to the stent location or shape relative to the vessels (as such has already been ensured). In the past, the flared portion of the stent had to be manually formed and located in the ostial region O, which was often difficult, unpredictable, and time consuming.

Turning to FIGS. 9-22, other preferred embodiments of the present invention are depicted. For the sake of brevity, the remaining description will focus primarily on the differences of these alternative embodiments from the preferred embodiment described above.

Turning to FIGS. 9-12, an alternative ostial stent 200 is constructed in accordance with a second embodiment of the present invention. The ostial stent 200 preferably comprises a tube 201 having a balloon-expandable distal tube section 202 and a self-expandable proximal tube section 204, with the tube sections 202,204 in partial overlapping engagement with one another. The ostial stent 200 is flared along the axis thereof to conform and, if desired, distend the ostial region O.

The distal tube section 202 preferably extends continuously between opposite proximal and distal ends 206,208 thereof (see FIGS. 9 and 10). However, it is within the scope of the present invention where distal tube section 202 is alternatively constructed. For instance, the distal tube section 202 could present a plurality of longitudinal slots that are spaced circumferentially and extend from either end 206,208 so that the distal tube section 202 presents multiple longitudinal legs. Also, the distal tube section 202 presents inner and outer distal tube diameter dimensions. The distal tube section 202 is preferably formed from laser-cut metal tube so that the distal tube section 202 can be manually expanded using a balloon (or another suitable stent-expanding device). The laser-cut metal tube preferably includes chromium-cobalt. As previously noted, the manner in which the tube is formed and the material from which it is formed may be varied without departing from the spirit of the present invention. The distal tube section 202 is preferably shiftable from a radially contracted condition (see FIGS. 9 and 10) to a radially expanded condition (see FIGS. 11 and 12). In both conditions, the outer tube diameter dimension of the tube section 202 is preferably substantially constant along the tube length.

The proximal tube section 204 preferably extends continuously between opposite proximal and distal ends 210, 212 thereof. Moreover, in the present embodiment, the proximal tube section 204 extends the full length of the stent 200 so as to define proximal and distal stent openings 213 and 214. The proximal tube section 204 presents inner and outer proximal tube diameter dimensions. However, it is within the scope of the present invention where proximal tube section 204 is alternatively constructed. For instance, the proximal tube section 204 could present a plurality of longitudinal slots that are spaced circumferentially and extend from either end 210,212 so that the proximal tube section 204 presents multiple longitudinal legs (as will be described). The proximal tube section 204 is also preferably formed of a laser-cut metal tube. The metal material of the proximal tube section 204 preferably includes Nitinol, although the proximal tube section could include another SMA material. Similar to proximal tube section 58, the proximal tube section 204 is preferably formed of Nitinol so that the proximal tube section 204 can be sufficiently expanded to at least conform to the shape of the associated vascular structure and, more preferably, even slightly distend the ostial region O.

The proximal tube section 204 preferably self-expands from a radially contracted condition (see FIGS. 9 and 10) to a memory flared condition (see FIGS. 11 and 12) when located adjacent the ostial region O. In particular, the tube section 204 is preferably flared outwardly toward the end 210 so that the end 210 engages the ostium O.

The tube sections 202,204 are preferably joined by partially overlapping the tube sections with one another so that the tube sections are in frictional engagement. In particular, the proximal tube section 204 preferably extends within the distal tube section 202 so that the entire length of the distal tube section 202 radially overlaps the proximal tube section 204 and defines a distal overlapping region of the tube section 204. That is, the overlapping region of the proximal tube section 204 is coextensive with the distal tube section 202. However, it is also within the scope of the present invention where the proximal tube section 204 is overlapped by the distal tube section 202 but only extends along part of the length of the distal tube section 202, as will be shown in a subsequent embodiment. Preferably, the overlapping region of the proximal tube section 204 has a circumferentially continuous shape and is substantially cylindrical.

Furthermore, the tube sections 202,204 are also preferably welded to one another along the overlapping region. However, the principles of the present invention are equally applicable where the tube sections 202,204 are solely attached to one another by welding or by frictional overlapping engagement. In this manner, the tube sections 202,204 are preferably held together for implantation along the ostium O until endotheliosis around the ostial stent 200 secures the ostial stent 200 in place.

As with the stent 22, the proximal tube section 204 is preferably flared outwardly toward the end 210 so that the end 210 engages the ostium O. The flared stent shape conforms closely to the region of the ostial wall and is configured to engage and buttress the ostial wall while restricting inadvertent stent movement into or out of the ostium O. The distal overlapping region of tube section 204 also expands outwardly as discussed below.

Figure 12:
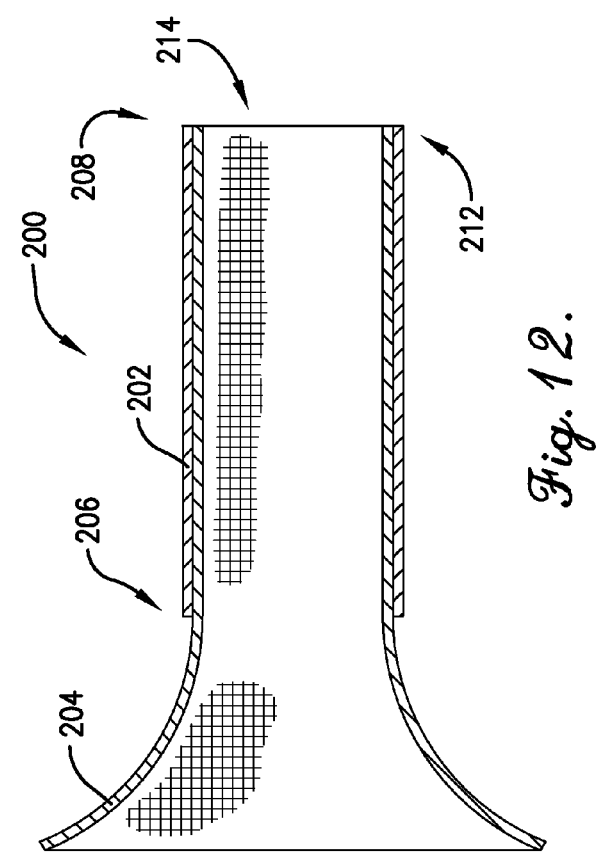
FIG. 12 is a longitudinal cross section of the ostial stent similar to FIG. 9, but showing the ostial stent in the memory flared condition, with the portion of the proximal tube section remaining coextensive with the distal tube section and the distal tube section fully radially overlapping the portion of the proximal tube section.
Figure 11:
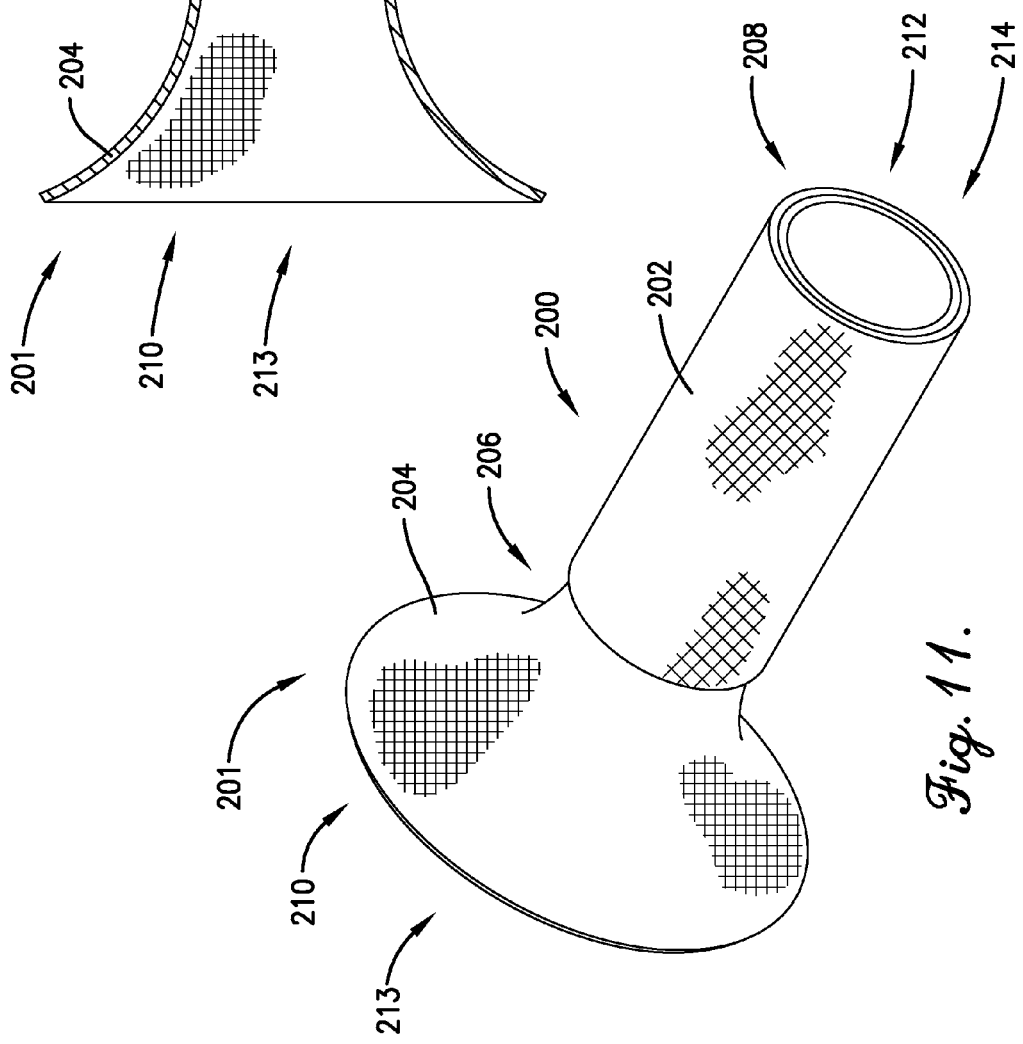
FIG. 11 is a perspective of the ostial stent similar to FIG. 8, but showing the ostial stent in a memory flared condition where the inner and outer tube diameters of the proximal tube section increase proximally from a location adjacent the proximal end of the distal tube section.

The distal tube section 202 and the overlapping region of tube section 204 are expanded into engagement with the renal artery by selective expansion from the radially contracted condition to the radially expanded condition. Preferably, a balloon is inflated to apply an expansion pressure within the distal tube section 202 to provide the desired tube expansion. Preferably, as depicted in FIGS. 11 and 12, the combination of the distal tube section 202 and the overlapping region of tube section 204 has substantially no flaring along the length thereof in the radially distended condition. However, for some aspects of the present invention, the combination of the distal tube section 202 and the overlapping region of tube section 204 could be flared in the radially expanded condition. For instance, the combination of the distal tube section 202 and the overlapping region of tube section 204 could be flared toward the proximal end 206 of the distal tube section 202 or toward the distal end 208 of the distal tube section 202.

Figure 14:
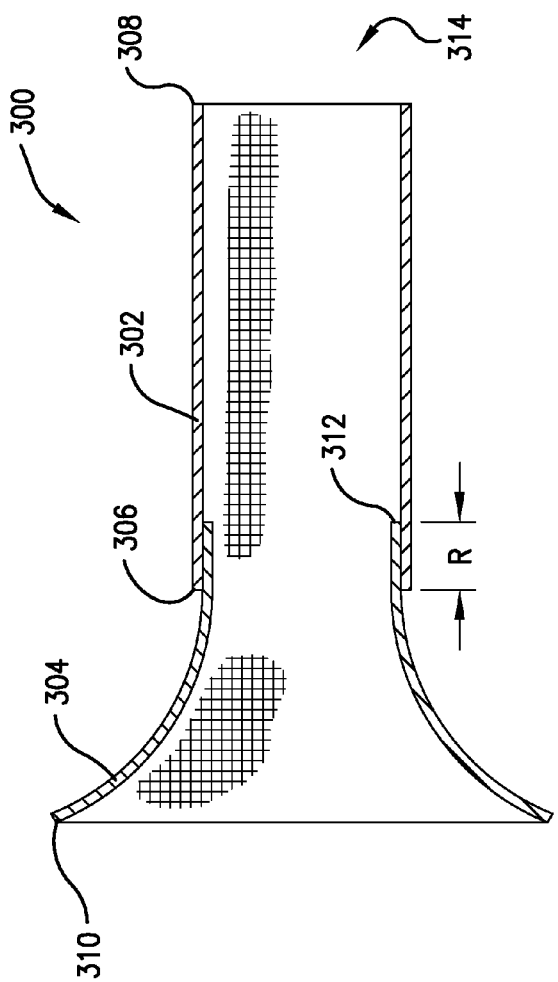
FIG. 14 is a longitudinal cross section of the ostial stent shown in FIG. 13, showing the proximal tube section extending part of the length of the distal tube section.
Figure 13:
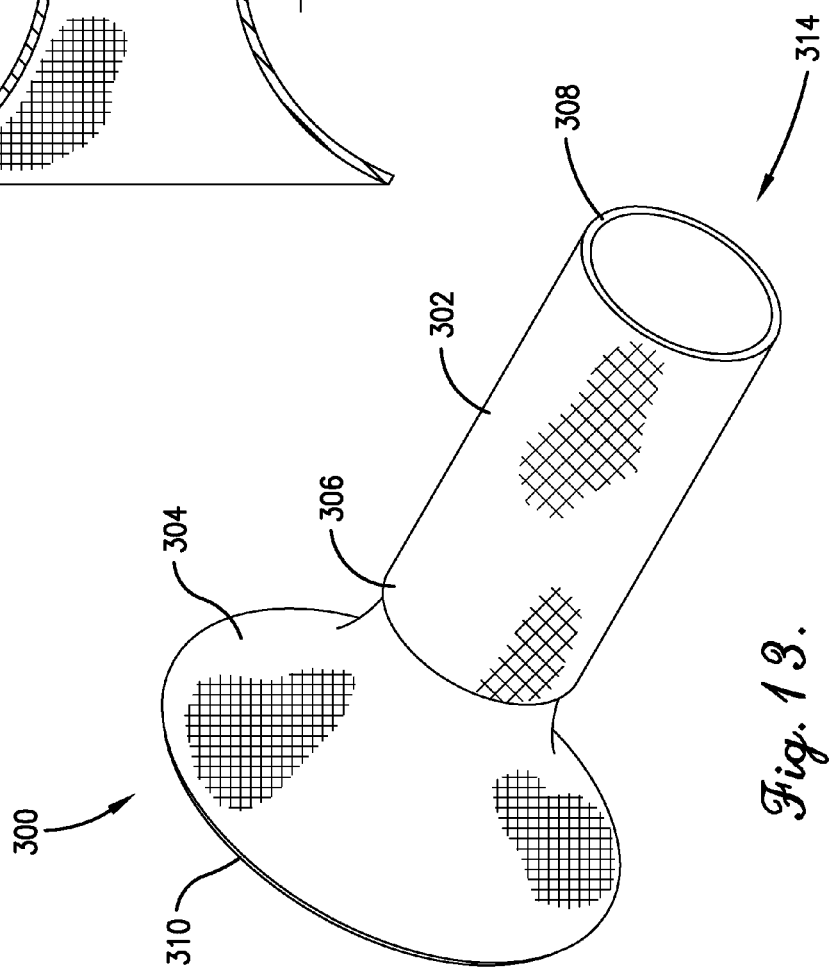
FIG. 13 is a perspective of an ostial stent constructed in accordance with a third preferred embodiment of the present invention, with the ostial stent including a self-expandable SMA proximal tube section and a balloon-expandable distal tube section that receives a portion of the proximal tube section.

Turning to FIGS. 13 and 14, an alternative ostial stent 300 is constructed in accordance with a third embodiment of the present invention. The ostial stent 300 preferably includes a balloon-expandable distal tube section 302 and a self-expandable proximal tube section 304, with the tube sections 302,304 in partial overlapping engagement with one another. The ostial stent 300 is flared along the axis thereof to distend the ostial region O.

The distal tube section 302 preferably extends continuously between opposite proximal and distal ends 306,308 thereof. The distal tube section 302 is preferably formed from laser-cut metal tube so that the distal tube section 302 can be selectively expanded using a balloon (or another suitable stent-expanding device). The laser-cut metal tube preferably includes chromium-cobalt. As previously noted, the manner in which the tube is formed and the material from which it is formed may be varied without departing from the spirit of the present invention. The distal tube section 302 is preferably shiftable from a radially contracted condition (not shown) to a radially expanded condition (see FIGS. 13 and 14). In both conditions, the outer tube diameter dimension of the tube section 302 is preferably substantially constant along the tube length.

The proximal tube section 304 preferably extends continuously between opposite proximal and distal ends 310, 312 thereof. The proximal tube section 304 presents inner and outer proximal tube diameter dimensions. The proximal tube section 304 is also preferably formed of a laser-cut metal tube. The metal material of the proximal tube section 304 preferably includes Nitinol, although the proximal tube section could include another SMA material. Similar to proximal tube section 58, the proximal tube section 304 is preferably formed of Nitinol so that the proximal tube section 304 can be sufficiently expanded to at least conform to the shape of the associated vascular structure and, more preferably, even slightly distend the ostial region O.

The proximal tube section 304 preferably automatically self-expands from a radially contracted condition (not shown) to a memory flared condition (see FIGS. 13 and 14) when located adjacent the ostial region O. In particular, the tube section 304 is preferably flared outwardly toward the end 310 so that the end 310 engages the ostium O.

The tube sections 302,304 are preferably joined by partially overlapping the tube sections with one another so that the tube sections are in frictional engagement. In particular, the proximal tube section 304 preferably extends axially within and is radially overlapped by the distal tube section 302 so as to define an overlapping region R. Furthermore, the tube sections 302,304 are also preferably welded to one another along the overlapping region R. However, the principles of the present invention are equally applicable where the tube sections 302,304 are solely attached to one another by welding or by frictional overlapping engagement. Preferably, the overlapping region R of the proximal tube section 304 has a circumferentially continuous shape and is substantially cylindrical. Preferably, the overlapping region R is spaced between the distal end 308 and the proximal end 310. That is to say, distal end 312 of the proximal tube section 304 is preferably spaced from a distal opening 314 so as to extend only partly inside the distal tube section 302.

The distal tube section 302 and the overlapping region R of tube section 304 are expanded into engagement with the renal artery by selective expansion from the radially contracted condition to the radially expanded condition. Preferably, a balloon is inflated to apply an expansion pressure within the distal tube section 302 to provide the desired tube expansion. Preferably, the combination of the distal tube section 302 and the overlapping region R of tube section 304 has substantially no flaring along the length thereof in the radially distended condition.

Figure 17:
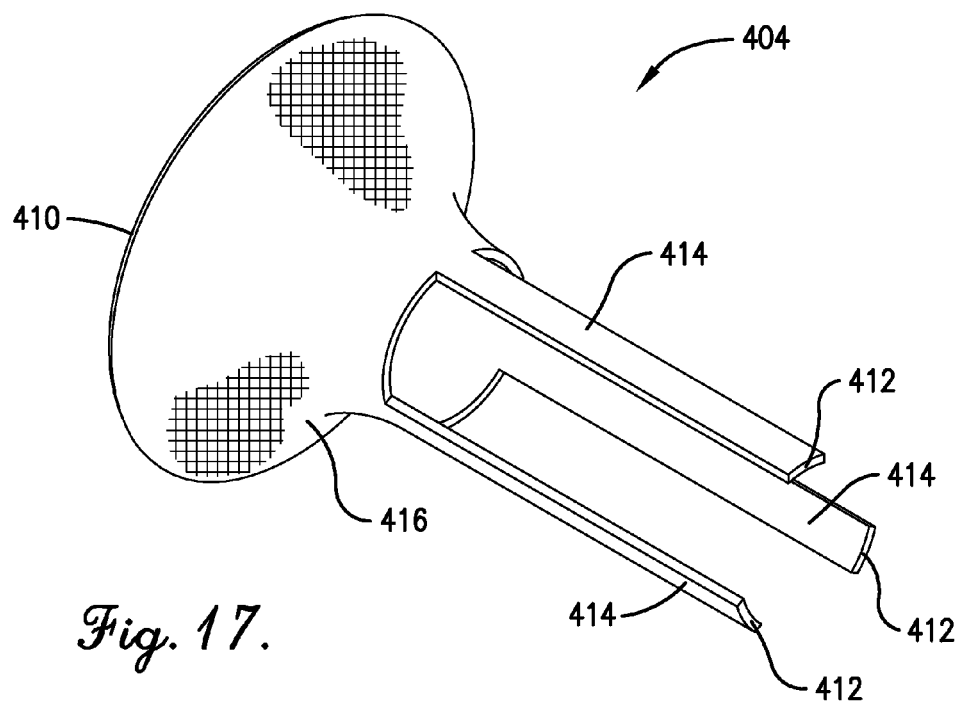
FIG. 17 is a perspective of the self-expandable SMA proximal tube section shown in FIGS. 15 and 16, showing the legs spaced circumferentially about an axis of the ostial stent and projecting distally from a body of the proximal tube section.

Turning to FIGS. 15-17, an alternative ostial stent 400 is constructed in accordance with a fourth embodiment of the present invention. The ostial stent 400 preferably includes a balloon-expandable distal tube section 402 and a self-expandable proximal tube section 404, with the tube sections 402,404 in partial overlapping engagement with one another.

The distal tube section 402 preferably extends continuously between opposite proximal and distal ends 406,408 thereof. The distal tube section 402 is preferably formed from laser-cut metal tube so that the distal tube section 402 can be manually expanded using a balloon (or another suitable stent-expanding device). The distal tube section 402 is preferably shiftable from a radially contracted condition (not shown) to a radially expanded condition (see FIGS. 15 and 16).

The proximal tube section 404 preferably extends continuously between opposite proximal and distal ends 410, 412 thereof. The proximal tube section 404 preferably includes multiple distal legs 414 that project from a continuous annular body 416 to the distal end 412 (see FIG. 17). The legs 414 are circumferentially spaced apart from one another about the axis of the proximal tube section 404 and are integrally formed with the body 416. The proximal tube section 404 is also preferably formed of a laser-cut metal tube. As previously noted, the manner in which the tube is formed and the material from which it is formed may be varied without departing from the spirit of the present invention. The metal material of the proximal tube section 404 preferably comprises Nitinol, although the proximal tube section could include another SMA material.

The tube sections 402,404 are preferably joined by partially overlapping the tube sections with one another so that the tube sections are in frictional engagement. The legs 414 of the proximal tube section 404 preferably extend axially within and are radially overlapped by the distal tube section 402 so as to define an overlapping region R that extends along the entire length of the distal tube section 402.

Preferably, the legs 414 and the distal tube section 402 are substantially coextensive with one another, although the principles of the present invention are equally applicable where the legs 414 are relatively shorter than the distal tube section 402. The tube sections 402,404 are preferably welded to one another along the overlapping region R, although only frictional engagement between the tube sections 402,404 can be used to interconnect them.

The ostial stent 400 is expanded into engagement with the renal artery by inflating a balloon to apply an expansion pressure within the distal tube section 402 to provide the desired tube expansion.

Figure 18:
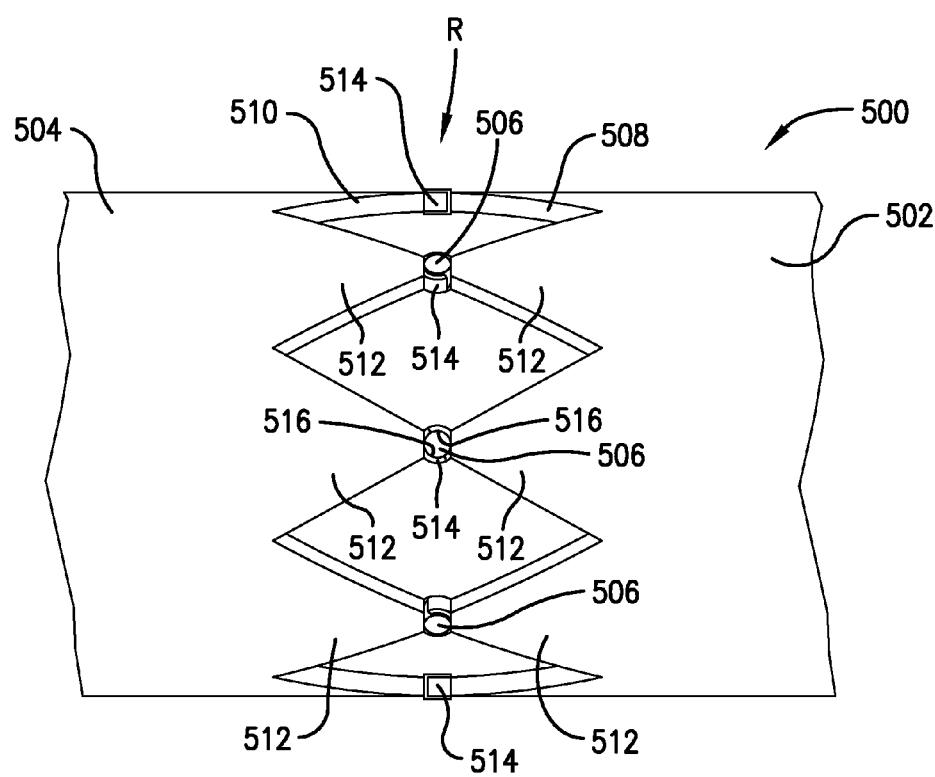
FIG. 18 is a fragmentary side elevation of an ostial stent constructed in accordance with a fifth preferred embodiment of the present invention, with the ostial stent including a self-expandable SMA proximal tube section, a balloon-expandable distal tube section, and circular connection disks, where each the tube sections include arms that radially overlap one another and are welded to the disks.

Turning to FIG. 18, an alternative ostial stent 500 is constructed in accordance with a fifth embodiment of the present invention. The ostial stent 500 preferably includes a balloon-expandable distal tube section 502 and a self-expandable proximal tube section 504 arranged in an end-to-end relationship, with the tube sections 502,504 being shown schematically. The ostial stent 500 also includes circular disks 506.

The tube sections 502,504 preferably present corresponding tube connection ends 508,510. The tube connection ends 508,510 each include a plurality of circumferentially spaced apart projections 512 and connection arms 514 that extend longitudinally from the projections 512. Each arm 514 is curved and presents a concave face 516 that is shaped to receive a corresponding circular disk 506. Each arm 514 preferably projects from the body of the corresponding tube section 502,504. Each of the tube sections 502,504 (including the projections 512 and arms 514) is preferably formed from a laser-cut metal tube. As previously noted, the manner in which each of the tubes is formed and the material from which it is formed may be varied without departing from the spirit of the present invention.

The circular disk 506 is unitary and preferably includes a material that is weldable to the tube sections 502,504. Preferably, the material of the circular disk 506 includes Tantalum or Niobium, although an alternative material (e.g., another material that is dissimilar from the material of the tube sections 502,504) may be used without departing from the scope of the present invention.

The tube sections 502,504 are preferably joined by welding the arms 514 of the tube sections 502,504 relative to one another. Specifically, each arm 514 of the tube section 502 and the corresponding arm 514 of the tube section 504 are paired with one another to present opposed faces 516 that cooperatively engage and capture a corresponding one of the disks 506. While each pair of arms 514 have opposed faces 516 that are spaced apart from one another in a circumferential direction, the disk 506 spans the gap formed between the pair of opposed faces 516. Each pair of arms 514 is then welded to the corresponding disk 506. It may be said that the arms 514 overlap one another along a longitudinal direction to define an overlapping region R spaced from the outermost ends (not shown) of the ostial stent 500.

Turning to FIG. 19, an alternative ostial stent 600 is constructed in accordance with a sixth embodiment of the present invention. The ostial stent 600 preferably includes a balloon-expandable distal tube section 602, a self-expandable proximal tube section 604, and circular disks 606, with the tube sections 602,604 being shown schematically. The tube sections 602,604 are preferably arranged in an end-to-end configuration.

The tube sections 602,604 preferably present corresponding tube connection ends 608,610. The tube connection ends 608,610 each include a plurality of circumferentially spaced apart projections 612 and connection arms 614 that extend longitudinally from the projections 612. Each arm 614 presents opposite arm ends. Each arm 614 is curved and presents a concave face 616 that is shaped to receive a corresponding one of the circular disks 606. The tube sections 602,604 are each preferably formed from a laser-cut metal tube. As previously noted, the manner in which each of the tubes is formed and the material from which it is formed may be varied without departing from the spirit of the present invention.

Each circular disk 606 is unitary and preferably includes a material that is weldable to the tube sections 602,604. Preferably, the material of the circular disk 606 includes Tantalum or Niobium, but could include an alternative material without departing from the scope of the present invention.

The tube sections 602,604 are preferably joined by welding the arms 614 of the tube sections 602,604 relative to one another. Specifically, each arm 614 of the tube section 602 and the corresponding arm 614 of the tube section 604 are paired with one another, with corresponding arm ends being adjacent to one another. Each arm 614 of the tube section 602 and the corresponding arm 614 of the tube section 604 are paired to present opposed faces 616 that cooperatively engage and capture a corresponding one of the disks 606. While each pair of arms 614 have opposed faces 616 that are spaced apart from one another in a longitudinal direction, the disk 606 spans the gap formed between the pair of opposed faces 616. Each pair of arms 614 is then welded to the corresponding disk 606. Each pair of arms 614 is positioned adjacent to one another, although the arms 614 of each pair preferably do not radially overlap one another. Generally, the tube sections 602,604 are positioned end-to-end to avoid any radial overlap therebetween.

Turning to FIG. 20, an alternative ostial stent 700 is constructed in accordance with a seventh embodiment of the present invention. The ostial stent 700 preferably includes a balloon-expandable distal tube section 702, a self-expandable proximal tube section 704, and discrete stitches 706, with the tube sections 702,704 being shown schematically.

The tube sections 702,704 preferably present corresponding tube connection ends 708,710. The tube connection ends 708,710 each include a plurality of circumferentially spaced apart projections 712 and adjacent openings 714.

The tube sections 702,704 are preferably joined by securing the tube sections 702,704 to one another with stitches 706. Specifically, a series of stitches 706 are spaced circumferentially about the ostial stent 700. The stitches 706 are threaded through the openings 714 to secure a corresponding pair of projections 712 to one another. Generally, the tube sections 702,704 are positioned end-to-end to avoid any radial overlap therebetween.

The stitches 706 can preferably include a metallic material or a nonmetallic material. Metallic materials suitable for use as stitches 706 preferably include gold and tantalum, but could other metallic materials. Nonmetallic materials to provide stitches 706 preferably include Dacron®, PTFE, Small Intestine Submucosa (SIS), or ceramic. However, it is within the scope of the present invention where nonmetallic stitches include yet another synthetic resin material, such as an alternative polymer.

Turning to FIG. 21, an alternative ostial stent 800 is constructed in accordance with an eighth embodiment of the present invention. The ostial stent 800 preferably includes a balloon-expandable distal tube section 802, a self-expandable proximal tube section 804, discrete stitches 806, and an intermediate tube section 808, with the tube sections 802, 804,808 being shown schematically.

The tube sections 802,804 preferably present corresponding tube connection ends 810,812. The tube connection ends 810,812 each include a plurality of circumferentially spaced apart projections 814. Generally, the tube sections 802,804, 808 are positioned end-to-end to avoid any radial overlap therebetween.

The intermediate tube section 808 presents tube connection ends 818,820. The tube connection ends 818,820 also present spaced apart projections 822. The tube section 808 preferably includes a woven fabric, where the fabric includes a nonmetallic material such as Dacron®, PTFE, or Small Intestine Submucosa (SIS). The tube section 808 is preferably flexible to permit limited relative movement between the tube sections 802,804. However, it is within the ambit of the present invention where the tube section 808 includes an alternative material such as silicon or rubber.

To position the tube sections 802,804,808 for joining, each projection 814 of one of the tube sections 802,804 is circumferentially interposed between adjacent projections 822 of the intermediate tube section 808. In this manner, the projections 814,822 of the tube sections 802,804,808 are circumferentially interdigitated.

The tube sections 802,804 are preferably joined relative to one another by securing the tube sections 802,804 to the intermediate tube section 808 with stitches 806. Specifically, one or more stitches 806 are threaded through openings presented by the projections 814,822 to secure the tube sections 802,804 to intermediate tube section 808. Again, the tube section 808 includes a flexible material such that the tube sections 802,804 can move relative to one another.

The various stent embodiments depicted in FIGS. 18-21 include connection structure spanning between the respective tube sections, with the connection structure being formed of a material dissimilar from that of the respective tube sections. It will be appreciated that alternative connection structures may be used without departing from the spirit of the present invention. For example, the stent may alternatively be provided with pin and socket connectors (not shown) at the junction between the tube sections. The connectors would essentially provide a snap-fit connection between the tube sections. Each complemental set of connectors would include a pin connector secured to one of the tube sections and a socket connector secured to the other tube section. Each of the tube sections would preferably include a plurality of circumferentially spaced connectors projecting from the corresponding end thereof (if desired, each tube section may be provided with both pin and socket connectors, as long as the other tube section has the opposite connector arrangement). When the tube sections are moved toward one another, each pin "snaps" into the corresponding socket. The connectors may be suitably secured to the respective tube section (e.g., crimped, welded, press-fit, etc.).

Turning to FIG. 22, an alternative ostial stent 900 is constructed in accordance with a ninth embodiment of the present invention. The ostial stent 900 preferably includes a balloon-expandable distal tube section 902 and a self-expandable proximal tube section 904, with the tube sections 902,904 being shown schematically.

The tube sections 902,904 preferably present corresponding tube connection ends 906,908. The tube connection ends 906,908 each include a plurality of circumferentially spaced apart longitudinal projections 910. To position the tube sections 902,904 for joining, each projection 910 of one of the tube sections 902,904 is circumferentially interposed between adjacent projections 910 of the other one of the tube sections 902,904. In this manner, the projections 910 of the tube sections 902,904 are circumferentially interdigitated and cooperatively form an overlapping region R. The tube sections 902,904 are preferably joined by welding the tube sections 902,904 to one another with a plurality of welds 912 located about the joint.

Although the above description presents features of preferred embodiments of the present invention, other preferred embodiments may also be created in keeping with the principles of the invention. Such other preferred embodiments may, for instance, be provided with features drawn from one or more of the embodiments described above. Yet further, such other preferred embodiments may include features from multiple embodiments described above, particularly where such features are compatible for use together despite having been presented independently as part of separate embodiments in the above description.

The preferred forms of the invention described above are to be used as illustration only, and should not be utilized in a limiting sense in interpreting the scope of the present invention. Obvious modifications to the exemplary embodiments, as hereinabove set forth, could be readily made by those skilled in the art without departing from the spirit of the present invention.

The inventor hereby states his intent to rely on the Doctrine of Equivalents to determine and assess the reasonably fair scope of the present invention as pertains to any apparatus not materially departing from but outside the literal scope of the invention as set forth in the following claims.

What is claimed is:

1. An ostial stent for placement at the ostium of a patient's vascular system so as to improve vessel patency in the ostial region, said ostial stent comprising:
    a stent tube presenting spaced apart proximal and distal stent openings and a longitudinal stent passage that extends between the openings,
    said stent tube including a selectively-expandable tube section and a self-expandable tube section,
    said self-expandable tube section projecting longitudinally from one of the stent openings, and being automatically expandable to a flared condition for placement within the ostium,
    said self-expandable tube section presenting opposite ends one of which defines said one of the stent openings,
    said self-expandable tube section presenting a sleeve shape that extends circumferentially around said one of the stent openings,
    said tube sections being partly overlapped and interconnected along an overlapping region,
    said overlapping region being spaced longitudinally from said one of the stent openings, such that the self-expandable tube section is at least partly outside the overlapping region,
    said self-expandable tube section including a plurality of circumferentially spaced apart legs, each of which is located radially inside the selectively-expandable tube section along the overlapping region.

2. The ostial stent as claimed in claim 1,
    said selectively-expandable tube section projecting longitudinally from the other one of the stent openings,
    said legs extending to the other one of the stent openings.

3. The ostial stent as claimed in claim 1,
    said tube sections being frictionally interengaged.

4. The ostial stent as claimed in claim 3,
    said tube sections being welded to each other.

5. The ostial stent as claimed in claim 1,
said self-expandable tube section comprising a shape memory alloy tube shaped in the high-temperature phase prior to patient insertion to form a flared pre-expanded tube shape, with the shape memory alloy tube being operable to contract from the pre-expanded tube shape toward a radially contracted condition when cooled.

6. The ostial stent as claimed in claim 1,
said self-expandable tube section including a woven fabric and/or a laser-cut tube shape memory alloy material.

7. The ostial stent as claimed in claim 6,
said woven fabric and/or a laser-cut tube shape memory alloy material being selected from the group consisting of nickel-titanium, copper-zinc-aluminum-nickel, copper-aluminum-nickel, and combinations thereof.

8. The ostial stent as claimed in claim 1,
said selectively-expandable tube section being expandable from a radially contracted condition to a radially distended condition by applying an expansion pressure within the selectively-expandable tube.

9. The ostial stent as claimed in claim 8,
said selectively-expandable tube section having a generally cylindrical shape in the radially distended condition so as to have substantially no flaring.

10. The ostial stent as claimed in claim 8,
said selectively-expandable tube section including a woven fabric and/or laser-cut tube material.

11. The ostial stent as claimed in claim 10,
said woven fabric and/or laser-cut tube material being selected from the group consisting of stainless steel, chromium-cobalt, Nuloy, Nitinol, a bioabsorbable polymer, a biocorrodable metal, and combinations thereof.

12. The ostial stent as claimed in claim 1,
said tube presenting an axis extending between the openings,
each of said legs being axially straight, such that each adjacent pair of legs defines an axially extending space therebetween that is substantially constant in an axial direction.

* * * * *